United States Patent [19]

Pellico et al.

[11] Patent Number: 4,564,519
[45] Date of Patent: * Jan. 14, 1986

[54] DI-ENZYMATIC CHEWABLE DENTIFRICE

[75] Inventors: Michael A. Pellico, Los Angeles; Robert E. Montgomery, Pacific Palisades, both of Calif.

[73] Assignee: Laclede Professional Products, Inc., Gardena, Calif.

[ * ] Notice: The portion of the term of this patent subsequent to May 26, 1998 has been disclaimed.

[21] Appl. No.: 559,474

[22] Filed: Dec. 8, 1983

Related U.S. Application Data

[63] Continuation-in-part of Ser. No. 501,383, Jun. 6, 1983, Pat. No. 4,537,764, which is a continuation-in-part of Ser. No. 292,633, Aug. 13, 1981.

[51] Int. Cl.[4] .......................... A61K 9/68; A61K 7/28; A61K 37/50
[52] U.S. Cl. .......................... 424/48; 424/50; 424/94
[58] Field of Search .............................. 424/48, 50, 94

[56] References Cited

U.S. PATENT DOCUMENTS

| | | | |
|---|---|---|---|
| 1,052,872 | 2/1913 | Williams | 424/48 |
| 1,171,392 | 2/1916 | Meier | 424/48 |
| 2,290,862 | 7/1942 | Canning | 424/48 |
| 2,891,868 | 6/1959 | Heggie et al. | 424/48 |
| 4,150,113 | 4/1979 | Hoogendoorn et al. | 424/50 |
| 4,178,362 | 12/1979 | Hoogendoorn et al. | 424/48 |
| 4,269,822 | 5/1981 | Pellico et al. | 424/50 |
| 4,302,441 | 11/1981 | Muhlemann et al. | 424/48 |
| 4,335,101 | 6/1982 | Stoudt et al. | 424/50 |
| 4,438,093 | 3/1984 | Shimada et al. | 424/50 |

OTHER PUBLICATIONS

Dixon et al, "Enzymes", Academic Press (1958) N.Y., pp. 184–185, 202–203, 284–287, 344–345; 354–355; 438–439; 682–683; 688–689; 706–707.
C.A., 37, #1467(4), #2036(8), #3789(3), #4421(1) (1943) 38, #137(6) (1944) 39, #526(1) (1945).
C.A., 40, #6546(6) (1946), 41, #2165c (1947), 42, #4636a, #4625d (1958) 43, #3857(1) (1949).
C.A., 44, #4055(1) (1950), C.A., 32, #721(2) (1938) 44, #6573, (1950) 46, #3852 (1) (1952).

Primary Examiner—Shep K. Rose
Attorney, Agent, or Firm—Donald Diamond

[57] ABSTRACT

A di-enzymatic chewable dentifrice is provided which contains an oxidizable substrate and an oxidoreductase enzyme specific to such substrate for producing hydrogen peroxide upon chewing of the dentifrice and further contains a thiocyanate salt and lactoperoxidase for interacting with hydrogen peroxide to produce a hypothiocyanate bacterial inhibitor. The concentration of lactoperoxidase is at least about 2% of the concentration of the oxidoreductase enzyme, in International Units, to thereby limit the ratio of hydrogen peroxide to lactoperoxidase during oral chewing of the dentifrice. An illustrative enzymatic system for this purpose contains glucose, glucose oxidase, potassium thiocyanate and lactoperoxidase.

18 Claims, No Drawings

DI-ENZYMATIC CHEWABLE DENTIFRICE

CROSS-REFERENCE TO RELATED APPLICATIONS

This application is a continuation-in-part of U.S. patent application Ser. No. 292,633, filed Aug. 13, 1981 and entitled Di-Enzymatic Dentifrice and is also a continuation-in-part of U.S. patent application Ser. Mo. 501,383, filed June 6, 1983 and entitled Stabilized Enzymatic Dentifrice Containing B-D-Glucose And Glucose Oxidase, now U.S. Pat. No. 4,537,764, which application, in turn, is a continuation-in-part of the aforesaid U.S. patent application Ser. No. 292,633.

BACKGROUND OF THE INVENTION

This invention relates to chewable dentifrice compositions and, more particularly, to chewable antiseptic dentifrice compositions wherein hypothiocyanate, a bacterial inhibitor, is produced in situ during oral chewing of the dentifrice.

The term "chewable dentifrice" as used herein refers to chewing gum, and chewable and orally soluble tablets, troches, lozenges, drops and the like.

Non-chewable dentifrices, in powder, paste, cream and liquid forms, are used for both cosmetic and therapeutic purposes. Consistent with these purposes, such dentifrices are formulated to contain active ingredients such as cleansing and polishing materials, as well as various antibacterial and anticaries agents for use as aids in the prevention of tooth decay. It is also suggested in the prior art that chewable dentifrices such as chewing gum and chewable tablets and lozenges be formulated with antiseptic-type compositions for beneficially effecting dental care.

It is generally understood in the dental art that certain kinds of tooth decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associated with the plaque, cause decalcification beneath the plaque matrix through metabolic activity which results in the accumulation and localized concentration of organic acids. The etching and decalcification of the enamel may continue until the pulp chamber of the tooth is reached.

A wide variety of materials have been considered for use as decay-preventative agents in dentifrice compositions. Some of the substances which have been so considered include para-aminobenzoic acid, a combination of urea and urease to produce ammonia during oral application of the dentifrice, chlorophyll, perfluorinated long chain organic compounds, complex iodine, penicillin, benzohydroxamic acid, and glucose oxidase to produce hydrogen peroxide during oral application of the dentifrice. Substances which have been considered in connection with chewable dentifrices include: carbolic acid, menthol, thymol and eucalypthus; peroxides and perborates such as calcium peroxide and sodium perborate; and glucose oxidase, an oxidoreductase enzyme, to produce hydrogen peroxide during oral chewing of the dentifrice.

U.S. Pat. No. 1,171,392 (Meier, 1916) discloses an antiseptic chewing gum comprising chicle, glucose and sugar together with an admixture of powdered chalk and an antiseptic such as carbolic acid, menthol, thymol or eucalypthus.

U.S. Pat. No. 2,290,862 (Canning, 1942) discloses an antiseptic chewing gum comprising chicle, glucose, flavoring material and sugar together with an admixture of hydrogenated peanut oil and calcium peroxide.

Commercial glucose oxidase which also contains catalase is promoted to the food and beverage industry as an agent for protecting their susceptible packaged products against deterioration in the presence of oxygen and/or glucose by effecting an enzymatic in situ reaction which results in the consumption of oxygen and glucose with an intermediate product being hydrogen peroxide and the ultimate end product of the enzymatic reaction being gluconic acid.

U.S. Pat. No. 2,891,868 (Heggie et al., 1959) discloses that chewing gum which is formulated with an oxygen sensitive flavoring agent can be protected against oxidative deterioration of the flavoring agent by incorporating into the formulation an enzyme system containing glucose, glucose oxidase and catalase, and that this protection is effective in the presence of bound water only and does not require free water.

U.S. Pat. No. 4,178,362 (Hoogendoorn et al., 1979) discloses an enzymatic chewable dentifrice containing glucose oxidase which acts on glucose present in saliva and tooth plaque to produce hydrogen peroxide. The patentees note that oral bacteria, through enzyme systems having SH-groups, effect glycolysis of food products containing sugars and point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

Morrison et al., Biology of the Mouth, American Association for the Advancement of Science, 1968, pp. 89–110 disclose: that lactoperoxidase, sodium thiocyanate and hydrogen peroxide define a bacterial inhibitory system; that in vivo production of hydrogen peroxide might be generated by microorganisms; and that the lactoperoxidase antimicrobiological system (which also includes hydrogen peroxide and thiocyanate) is reversed by catalase, which competes with lactoperoxidase for available hydrogen peroxide.

Hoogendoorn et al., Caries Research, 11:77–84, 1977, disclose that the hypothiocyanate ion is the bacterial inhibitor formed by the system containing lactoperoxdiase, thiocyanate and hydrogen peroxide and further disclose that a high concentration of hydrogen peroxide inactivates lactoperoxdiase.

Thomas et al., Journal of Dental Research, 60(4), pp. 785–796, April, 1981, disclose with respect to the salivary antimicrobial system consisting of peroxidase enzyme(s), hydrogen peroxide and thiocyanate ion: (a)

that peroxidase is synthesized by the salivary glands, (b) that production of hydrogen peroxide in saliva may be due to leucocytes or to oral bacteria primarily streptococci and lactobacilli, (c) that the salivary glands concentrate thiocyanate ion from blood and (d) that the antimicrobial activity of the peroxidase system is due to peroxidase catalyzed oxidation of thiocyanate ion (SCN) to hypothiocyanate ion (OSCN); and (e) further disclose that the yield or accumulation of hypothiocyanate from the aforesaid antimicrobial system can be increased by the presence of aminohexoses, namely, glucosamine and N-acetyl glucosamine.

The effectiveness of a glucose oxidase chewable dentifrice (U.S. Pat. No. 4,178,362) as a bacterial inhibitor through the production of hypothiocyanate is dependent, to a significant extent, upon the subsisting oral concentration of glucose, potassium thiocyanate and lactoperoxdiase as well as hydrogen peroxide at the time of oral chewing of the dentifrice. The concentration of those ingredients supplied by saliva, including potassium thiocyanate and lactoperoxdiase, varies as a direct function of biological production and salivary flow. Thus, when salivary flow is at a diminished level either as a natural event or as an event arising out of certain types of medical treatment, the oral concentration of potassium thiocyanate and lactoperoxdiase will be correspondingly reduced which, in turn, is a limiting factor in the oral production of hypothiocyanate bacterial inhibitor. Moreover, when the oral concentration of lactoperoxdiase is suppressed through diminished salivary flow, the oral concentration of hydrogen peroxide produced by the glucose oxidase/carbohydrase system, as described in U.S. Pat. No. 4,178,362, may rise to the threshold level which can impede the effectiveness of lactoperoxidiase. Accordingly, it would be advantageous to provide a substantially self-contained, hypothiocyanate generating, enzymatic chewable dentifrice which is not dependent upon the naturally occurring, oral concentration of glucose, potassium thiocyanate or lactoperoxidiase for antibacterial effectiveness, upon oral chewing of the dentifrice.

SUMMARY OF THE INVENTION

In accordance with this invention, there is provided a di-enzymatic chewable dentifrice containing, per gram of dentrifice, from about 0.015 to about 0.6 millimole of oxidizable substrate and from about 0.5 to about 500 International Units of an oxidoreductase enzyme specific to such substrate for producing hydrogen peroxide upon oral chewing of said dentifrice and further containing from about 0.0001 to about 0.01 millimole of a thiocyanate salt and from about 0.01 to about 50 International Units of lactoperoxidase for interacting with hydrogen peroxide to produce a hypothiocyanate bacterial inhibitor, wherein the concentration of lactoperoxdiase in International Units is at least about 2% of the concentration of the oxidoreductase enzyme in International Units to thereby limit the ratio of hydrogen peroxide to lactoperoxidase during oral chewing of the dentifrice.

DETAILED DESCRIPTION

The di-enzymatic chewable dentifrice of this invention comprises a first enzyme system containing an oxidizable substrate and an oxidoreductase enzyme specific to such substrate for producing hydrogen peroxide upon oral chewing of the dentifrice, with the chemical environment of the oral cavity providing the source of the additional reactant (oxygen) or reactants (oxygen, water) to effect the enzymatic reaction.

The components of the first enzyme system which can be incorporated into the chewable dentifrice compositions to produce hydrogen peroxide upon oral chewing of the dentifrice are illustrated by the substrate/enzyme combinations set forth in Table I.

TABLE I

| Oxidizable Substrate | Oxidoreductase Enzyme |
|---|---|
| (a) B-D-glucose | glucose oxidase |
| (b) D-galactose | galactose oxidase |
| (c) Urate | urate oxidase |
| (d) Choline | choline oxidase |
| (e) D-amino acids | D-amino acid oxidase |
| (f) D-glutamate | D-glutamate oxidase |
| (g) Glycine | glycine oxidase |
| (h) Glycollate | glyclollate oxidase |
| (i) L-sorbose | L-sorbose oxidase |
| (j) Primary alcohol | alcohol oxidase |
| (k) Primary amine | amine oxidase |

The reactions of representative enzyme systems from Table I, which are activated in the chemical environment of the oral cavity to produce hydrogen peroxide, are set forth in Table II.

TABLE II (a) Glucose oxidase catalyzes the interaction of Beta-D-glucose, water and oxygen to produce hydrogen peroxide and gluconic acid;

(b) Galactose oxidase catalyzes the interaction of D-galactose and oxygen to produce hydrogen peroxide and D-galacto-hexo-dialdose;

(c) Urate oxidase catalyzes the interaction of urate, water and oxygen to produce hydrogen peroxide, allantoin and carbon dioxide;

(d) Choline oxidase catalyzes the interaction of choline and oxygen to produce hydrogen peroxide and betaine aldehyde;

(e) D-amino acide oxidase catalyzes the interaction of D-amino acids such as the D isomers of proline, methionine, isoleucine, alanine, valine and phenylalanine together with water and oxygen to produce hydrogen peroxide, ammonia and the corresponding alpha-keto acids;

(f) D-glutamate oxidase catalyzes the interaction of D-glutamate, water and oxygen to produce hydrogen peroxide, ammonia and 2-oxoglutarate; and (g) Glycine oxidase catalyzes the interaction of glycine, water and oxygen to produce hydrogen peroxide, ammonia and glyoxylic acid.

The characteristics of representative oxidoreductase enzymes identified in Table I, from specific sources, are set forth in Table III.

TABLE III (a) Glucose oxidase from A. niger:

(i) Molecular weight; 150,000 (Pazur et al., 1965); 153,000 (Swoboda, 1969).

(ii) Composition: a glycoprotein containing two molecules of flavine-adenine dinucleotide (see: The Merck Index, 9th Ed., 1976, page 532, section 4007 and page 576, section 4291). The amino acid composition has been determined (Pazur et al., 1965).

(iii) Ioselectric point: pH 4.2.

(iv) Optimum pH: 5.5 with a broad pH range from 4 through 7.

(v) Inhibitors: monovalent silver and divalent mercury and copper ions.

(b) Galactose Oxidase from Dactylium Dendroides:
  (i) Molecular Weight: 42,000 (Kelly-Falcoz, 1965)
  (ii) Composition: metaloenzyme containing 1 gram atom of copper per mole (Amaral et al., 1963). The amino acid composition has been determined (Kelly-Falcoz, 1965).
  (iii) Optimum pH: 7 (Cooper et al., 1959).

(c) Urate Oxidase (uricase) from Hog Liver or Beef Liver:
  (i) Molecular Weight: 100,000 (Mahler et al., 1955).
  (ii) Composition: metaloenzyme containing 1 gram atom of copper per mole (Mahler, 1955).
  (iii) Isoelectric point: pH 6.3.
  (iv) Optimum pH: 9.

(d) D-Amino Acid Oxidase from Hog Kidney:
  (i) Molecular Weight: 90,000 (Antonini et al., 1966).
  (ii) Composition: A glycoprotein containing two molecules of flavine-adenine dinucleotide.
  (iii) Optimum pH: 9.
  (iv) Inhibitors: certain heavy metals.

The oxidizable substrate is generally present in the dentifrice in an amount from about 0.015 to about 0.6 millimole per gram of dentifrice and, preferably, from about 0.025 to about 0.1 millimole per gram of dentifrice while the oxidoreductase enzyme specific to the substrate is generally present in the dentifrice in an amount from about 0.5 to about 500 International Units (hereinafter sometimes abbreviated IU) per gram of dentifrice and preferably, from about 1.0 to about 40 IU per gram of dentifrice. The term millimole identifies that quantity in grams corresponding to the molecular weight of the composition divided by one thousand. The term International Unit(s) identifies that amount of enzyme that will effect catalysis of 1.0 micromole of substrate per minute at pH 7.0 and 25° C. Oxidoreductase enzymes are supplied in dry or liquid form with the label specifying the concentration in International Units on a per gram or per milliliter basis, as appropriate.

In addition to the first enzyme system comprising oxidizable substrate and oxidoreductase enzyme specific to such substrate for producing hydrogen peroxide, the di-enzymatic dentifrice of this invention is provided with a second enzyme system containing a thiocyanate salt and lactoperoxidase for interacting with hydrogen peroxide to produce a bacterial inhibitor in the form of a negative, monovalent hypothiocyanate ion (OSCN) which exists in solution in acid-base equilibrium with hydrogen hypothiocyanate (HOSCN).

The thiocyanate salts which can be used in the dentifrice include sodium thiocyanate, potassium thiocyanate, ammonium thiocyanate, ferric thiocyanate and mixtures thereof. The thiocyanate salt is generally present in the dentifrice in an amount from about 0.0001 to about 0.01 millimole per gram of dentifrice and, preferably, from about 0.001 to about 0.006 millimole per gram of dentifrice. Care should be taken in formulating the di-enzymatic dentifrice so as to avoid the use of metal compounds which inhibit or impair the effectiveness of oxidoreductase enzymes and/or peroxidase enzymes.

Lactoperoxidase is a glycoprotein which, in one commercial embodiment, is a lyophilized powder derived from milk. This commercial peroxidase has an activity of 80 IU/mg and a projected molecular weight of 93,000 for L-Tyrosine Iodination. The physical-chemical properties reported for lactoperoxidase include: molecular weight 78,000; partial specific volume 0.74; and heme/mole 1.0. Lactoperoxidase is generally present in the dentifrice in an amount from about 0.01 to about 50 IU per gram of dentifrice and, preferably, in an amount from about 0.2 to about 4.0 IU per gram of dentifrice.

In order to preserve the operable integrity of the di-enzymatic system, the ratio of hydrogen peroxide to lactoperoxidase should be limited, since excess hydrogen peroxide can inhibit lactoperoxidase. This limitation can be effected by providing a di-enzymatic system wherein the concentration of lactoperoxidase in International Units is at least about 2% of the concentration of the oxidoreductase enzyme in International Units. When the concentration of lactoperoxidase as a percentage of the oxidoreductase enzyme is below about 2%, the inhibition of lactoperoxidase becomes so rapid that the beneficial effects of the di-enzymatic system are terminated long before the end of the chewing cycle.

The operable integrity of the di-enzymatic system is also affected by catalase which is present in commercial glucose oxidase as well as oral surface tissue. Catalase, which is extraneous to the di-enzymatic system of this invention, competes with lactoperoxidase for hydrogen peroxide. In order to reduce loss of hydrogen peroxide through the presence of catalase, an effective amount of an enzymatic inhibitor specific to catalase can be advantageously incorporated into the di-enzymatic chewable dentifrice. An ascorbate salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of dentifrice. Iron salts such as ferrous sulfate can be incorporated into the di-enzymatic dentifrice as a potentiator for ascorbate salt in its role as catalase inhibitor.

The di-enzymatic dentifrice of this invention may advantageously be formulted with an aminohexose as, for example, an aminoglucose such as glucosamine, N-acetyl glucosamine or mixtures thereof in order to increase the yield or accumulation of the hypothiocyanate ion. The aminoglucose is generally present in the dentifrice in an amount from about 0.0001 to about 0.002 millimole per gram of dentifrice and, preferably, in an amount from about 0.0003 to about 0.001 millimole per gram of dentifrice.

Since water promotes the oxidation/reduction reactions of this invention and is also a reactant in certain reactions, the use of water in formulating the dentifrice compositions should be at a relatively low concentration level in order to impart maximum stability and shelf life to the compositions. For this purpose, it has been found to be essential to limit any unbound water present in the chewable dentifrice to an amount not more than about 1.0 wt.% and to limit the total water, bound and unbound, to not more than about 10 wt.%. A finely divided aqueous desicant such as silica aerogel may advantageously be included in the dentrifice in an amount from about 1 to about 5 wt. %.

Where the products of the activated enzyme system include a weak organic acid, it is advantageous to formulate the dentifrice with a buffering agent to neutralize the organic acid. A suitable buffering agent is sodium bicarbonate which can be present in the dentifrice in an amount up to about 6 wt. % as, for example, in an amount from about 4 to about 6 wt. %.

Formulations, equipment and processing techniques have been well developed in the art for preparing and packaging chewing gum and chewable tablets and lozenges. The di-enzymatic system of this invention is adapted to be incorporated into these formulations. However, the enzymes described herein are subject to degradation and inactivation under conditions such as high shear and elevated temperatures. Accordingly, processing conditions should be controlled during the time span that the enzymes are being admixed with the other ingredients of the formulation and converted into finished products so that the temperature does not rise above 55° C. for any extended period of time. In order to enhance shelf stability, the admixture used in the preparation of the di-enzymatic chewable dentifrice should be substantially free of unbound water and the finished product should be packaged in a manner so as to minimize exposure to air and moisture.

Illustrative base formulations for chewing gum and for chewable tablets and lozenges, which can be used in the preparation of the di-enzymatic chewable dentifrice, are set forth in Table IV as follows:

TABLE IV

| Ingredients | Weight Percent | | | |
|---|---|---|---|---|
| | (a) | (b) | (c) | (d) |
| Sorbitol, crystalline | 75 | — | 98 | 28 |
| Corn sugar | — | 75 | — | 70 |
| Gum base | 23 | 23 | — | — |
| Flavor | 1 | 1 | 1 | 1 |
| Color | 0.5 | 0.5 | 0.5 | 0.5 |
| Buffer | — | — | 0.5 | 0.5 |
| Saccharin, sodium | 0.005 | — | 0.005 | — |

In Table IV, formulations (a) and (b) illustrate chewing gum compositions while formulations (c) and (d) illustrate tablet and lozenge compositions. Aspartame can be substituted for sodium saccharin in these formulations.

EXAMPLE I

The following examples show varying ingredients and concentration levels which can be used in the preparation of di-enzymatic chewable dentifrices:

TABLE V

| | Weight, grams | | |
|---|---|---|---|
| | 5A | 5B | 5C |
| Chewing Gum | | | |
| Sorbitol, Cryst. | 70 | 70 | 70 |
| Gum base | 23 | 23 | 23 |
| Glycerol | 5 | 5 | 5 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |
| Di-Enzymatic System, (per 100 g chewing gum) | | | |
| Glucose oxidase | 40,000 IU | — | — |
| B-D glucose | 1.0 g | — | — |
| Choline oxidase | — | 8,000 IU | — |
| Choline | — | 1.0 g | — |
| D-Glutamate oxidase | — | — | 2,500 IU |
| D-Glutamate | — | — | 0.1 g |
| Lactoperoxidase | 4,000 IU | 1,500 IU | 1,000 IU |
| Potassium thiocyanate | 0.01 g | 0.005 g | — |
| Sodium thiocyanate | — | — | 0.01 g |

TABLE VI

| | Weight, grams | | |
|---|---|---|---|
| | 6A | 6B | 6C |
| Chewing Gum | | | |
| Sorbitol, cryst. | 43 | 43 | 43 |
| Corn sugar | 20 | 20 | 20 |
| Gum base | 25 | 25 | 25 |
| Flavor | 1 | 1 | 1 |
| Color | 0.5 | 0.5 | 0.5 |
| Sodium Bicarbonate | 0.5 | 0.5 | 0.5 |
| | 100.0 | 100.0 | 100.0 |
| Di-Enzymatic System, (per 100 g chewing gum) | | | |
| D-Amino acid oxidase | 5,000 IU | — | — |
| D-Alanine | 0.1 g | — | — |
| Glucose Oxidase | — | 20,000 IU | 2,000 IU |
| B-D-Glucose | — | 0.5 g | 0.5 g |
| Lactoperoxidase | 500 IU | 2,500 IU | 1,000 IU |
| Sodium thiocyanate | 0.01 g | — | — |
| Potassium thiocyanate | — | 0.01 g | 0.005 |
| Sodium ascorbate | — | 0.01 g | — |

TABLE VII

| | Weight, grams | | |
|---|---|---|---|
| | 7A | 7B | 7C |
| Lozenge | | | |
| Sorbitol, cryst. | 97 | 97 | 97 |
| Glycerol | 1.0 | 1.0 | 1.0 |
| Flavor | 1.0 | 1.0 | 1.0 |
| Color | 0.5 | 0.5 | 0.5 |
| Sodium bicarbonate | 0.5 | 0.5 | 0.5 |
| | 100.0 | 100.0 | 100.0 |
| Di-Enzymatic System, (per 100 g lozenge) | | | |
| Glucose oxidase | 10,000 IU | — | — |
| B-D-Glucose | 1 g | — | — |
| Urate oxidase | — | 10,000 IU | — |
| Urate | — | 0.75 g | — |
| Choline oxidase | — | — | 2,000 IU |
| Choline | — | — | 0.5 g |
| Lactoperoxidase | 200 IU | 200 IU | 1,500 IU |
| Sodium thiocyanate | 0.05 g | 0.08 g | — |
| Potassium thiocyanate | — | — | 0.01 g |

TABLE VIII

| | Weight, grams | | |
|---|---|---|---|
| | 8A | 8B | 8C |
| Lozenge | | | |
| Sorbitol, Cryst. | 80 | 80 | 80 |
| Corn sugar | 17 | 17 | 17 |
| Flavor | 1 | 1 | 1 |
| Color | 0.5 | 0.5 | 0.5 |
| Sodium bicarbonate | 0.5 | 0.5 | 0.5 |
| | 100.0 | 100.0 | 100.0 |
| Di-Enzymatic System, (per 100 g lozenge) | | | |
| D-Glutamate oxidase | 10,000 IU | — | — |
| D-Glutamate | 0.05 g | — | — |
| Glucose oxidase | — | 5,000 IU | 1,000 IU |
| B-D-Glucose | — | 0.5 g | 1 g |
| Lactoperoxidase | 1,500 IU | 2,000 IU | 1,000 IU |
| Potassium thiocyanate | 0.001 g | 0.005 g | — |
| Sodium thiocyanate | — | — | 0.005 g |

EXAMPLE II

This example shows the antibacterial effectiveness of the di-enzymatic chewable dentifrice of this invention. A di-enzymatic chewing gum was prepared having the following formulation:

| Composition | Weight, grams |
| --- | --- |
| Gum Base | 23 |
| Sorbitol, Cryst. | 75 |
| Color | 0.5 |
| Flavor | 1.0 |
| Beta-D-Glucose | 0.5 |
| Potassium thiocyanate | 0.01 |
| Glucose oxidase (100,000 IU/g) | 0.006 (600 IU) |
| Lactoperoxidase (100,000 IU/g) | 0.0006 (60 IU) |

The above composition was formed into sticks, each of which weighed 3 grams. Each of 5 individuals in Group (a) was given a stick of the gum with instructions to chew the gum for 10 minutes. Saliva samples were separately collected from the individuals in accordance with the following time sequence: individual 1, immediately after the chewing cycle; individual 2, 60 minutes after the chewing cycle; individual 3, 120 minutes after the chewing cycle; individual 4, 180 minutes after the chewing cycle; and individual 5, 240 minutes after the chewing cycle.

Five bacterial specimens were prepared by pouring 10 ml of Brain-Heart Infusion agar containing 10,000 colony units of streptococcus mutans (strain C67-1) into each of 5 Petri dishes.

Promptly following the collection of saliva from each individual, a 5 milliliter portion of the saliva was added with stirring to a Petri dish containing the bacterial specimens and the resulting admixture was incubated in an oven at 35° C. for 10 minutes. Upon completion of the incubation period, the bacterial specimen admixture was removed from the oven and microscopically evaluated for bacterial inhibition as determined by visible colony count. The foregoing procedure was repeated with 5 individuals in Group (b) except that the chewing gum contained gum base, sorbitol, color and flavor and did not include the di-enzymatic system. The results of this study are set forth in Table IX.

TABLE IX

| (a) | (b) | Time, minutes after chewing cycle when saliva added to bacterial broth | Bacterial Inhibition, %* (a) | (b) |
| --- | --- | --- | --- | --- |
| (control) | | (no chewing) | 0 | — |
| 1a | 1b | immediately | 99 | 37 |
| 2a | 2b | 60 | 99 | 12 |
| 3a | 3b | 120 | 98 | 2 |
| 4a | 4b | 180 | 97 | 0 |
| 5a | 5b | 240 | 96 | 0 |

*Percent bacterial inhibition indicates decrease in bacterial colonies compared to control count.

In view of the foregoing description and examples, it will become apparent to those of ordinary skill in the art that equivalent modifications thereof may be made without departing from the spirit and scope of this invention.

That which is claimed is:

1. A di-enzymatic chewable dentifrice containing, per gram of dentifrice, from about 0.015 to about 0.6 millimole of oxidizable substrate and from about 0.5 to about 500 International Units of an oxidoreductase enzyme specific to such substrate for producing hydrogen peroxide upon oral chewing of said dentifrice and further containing from about 0.0001 to about 0.01 millimole of a thiocyanate salt and from about 0.01 to about 50 International Units of lactoperoxidase for interacting with hydrogen peroxide to produce a hypothiocyanate bacterial inhibitor, wherein the concentration of lactoperoxidase in International Units is at least about 2% of the concentration of the oxidoreductase enzyme in International Units to thereby limit the ratio of hydrogen peroxide to lactoperoxidase during oral chewing of the dentifrice.

2. The dentifrice of claim 1 wherein the oxidizable substrate is Beta-D-glucose and the oxidoreductase enzyme is glucose oxidase.

3. The dentifrice of claim 1 wherein the oxidizable substrate is D-galactose and the oxidoreductase enzyme is galactose oxidase.

4. The dentifrice of claim 1 wherein the oxidizable substrate is urate and the oxidoreducatase enzyme is urate oxidase.

5. The dentifrice of claim 1 wherein the oxidizable substrate is choline and the oxidoreductase enzyme is choline oxidase.

6. The dentifrice of claim 1 wherein the oxidizable substrate is D-amino acid selected from the group consisting of D isomers of proline, methionine, isoleucine, alanine, valine and phenylalanine and the oxidoreductase enzyme is D-amino acid oxidase.

7. The dentifrice of claim 1 wherein the substrate is D-glutamate and the oxidoreductase enzyme is D-glutamate oxidase.

8. The dentifrice of claim 1 wherein the oxidizable substrate is glycine and the oxidoreductase enzyme is glycine oxidase.

9. The dentifrice of claim 1 wherein the thiocyanate salt is a member selected from the group consisting of sodium thiocyanate, potassium thiocyanate, ammonium thiocyanate and mixture thereof.

10. The dentifrice of claim 1 which also contains an aminoglucose selected from the group consisting of glucosamine, N-acetyl glucosamine and mixture thereof in an amount from about 0.001 to about 0.002 millimole per gram of dentifrice.

11. The dentifrice of claim 1 wherein the oxidizable substrate is present in an amount from about 0.025 to about 0.1 millimole per gram of dentrifice.

12. The dentifrice of claim 1 wherein the oxidoreductase enzyme is present in an amount from about 1 to about 40 International Units and lactoperoxidase is present in an amount from about 0.2 to about 4.0 International Units, per gram of dentifrice.

13. The dentifrice of claim 1 wherein the thiocyanate salt is present in an amount from about 0.001 to about 0.006 millimole per gram of dentifrice.

14. The dentifrice of claim 10 wherein the aminoglucose is present in amount from about 0.0003 to about 0.001 millimole per gram of dentifrice.

15. The dentrifice of claim 1 which also contains an effective amount of an enzymatic inhibitor specific to catalase, said enzymatic inhibitor being an ascorbate salt selected from the group consisting of sodium ascorbate, potassium ascorbate, ascorbyl palmitate, and mixtures thereof.

16. The dentifrice of claim 15 wherein the ascorbate salt is present in an amount from about 0.000001 to about 0.0001 millimole per gram of dentrifice.

17. The dentifrice of claim 1 wherein the oxidizable substrate is glucose which is present in an amount from about 0.025 to about 0.1 millimole per gram of dentifrice, the oxidoreductase enzyme is glucose oxidase which is present in amount from about 1 to about 40 International Units per gram of dentifrice, the thiocyanate salt is present in an amount from about 0.001 to about 0.0006 millimole per gram of dentifrice, and lactoperoxidase is present in an amount from about 0.2 to about 4.0 International Units per gram of dentifrice.

18. The dentifrice of claim 16 which also contains an aminoglucose selected from a group consisting of glucosamine, N-acetyl glucosamine and mixture thereof in an amount from about 0.0003 to about 0.001 millimole per gram of dentifrice.

* * * * *